United States Patent
Mukoh et al.

Patent Number: 4,479,885
Date of Patent: Oct. 30, 1984

[54] PHTHALONITRILE DERIVATIVES AND A LIQUID CRYSTAL COMPOSITION CONTAINING THE SAME

[75] Inventors: Akio Mukoh; Teruo Kitamura, both of Ibaraki; Masaharu Kaneko, Kanagawa; Tetsuo Ozawa, Tokyo, all of Japan

[73] Assignees: Hitachi Limited; Mitsubishi Chemical Industries Limited, both of Japan

[21] Appl. No.: 469,661

[22] Filed: Feb. 25, 1983

[30] Foreign Application Priority Data

Feb. 25, 1982 [JP] Japan ................... 57-29444

[51] Int. Cl.³ ..................... C09K 3/34; C07C 121/60
[52] U.S. Cl. ..................... 252/299.62; 252/299.63; 252/299.66
[58] Field of Search .......... 260/465 H, 465 F, 465 G; 252/299.62, 299.63, 299.66

[56] References Cited

U.S. PATENT DOCUMENTS 4,279,770  7/1981  Inubai ..................... 252/299.62
4,368,135  1/1983  Osman ..................... 252/299.63

Primary Examiner—Dolph H. Torrence
Attorney, Agent, or Firm—Sughrue, Mion, Zinn, Macpeak and Seas

[57] ABSTRACT

Phthalonitrile derivatives represented by the formula (I):

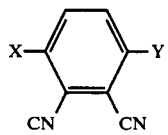

(wherein X and Y each represents an alkyl group having 1 to 9 carbon atoms, an alkoxy group havng 1 to 9 carbon atoms,

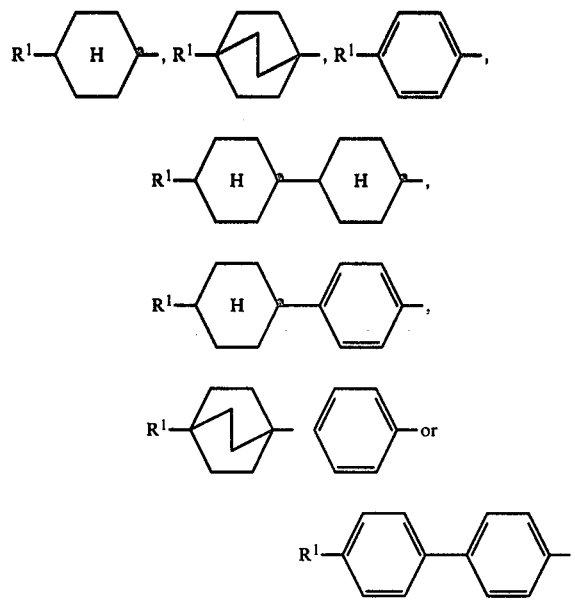

(wherein $R^1$ represents a hydrogen atom, $-C_mH_{2m+1}$, $-O-(CH_2CH_2O)_n-C_mH_{2m+1}$,

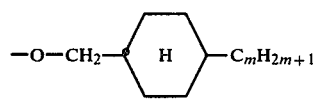

or a halogen atom, wherein m represents an integer of 1 to 9 and n represents 0, 1 or 2), but at least one of X and Y does not represent a methyl group, and Y does not not represent an alkyl group having 1 to 9 carbon atoms or an alkoxy group having 1 to 9 carbon atoms in the case that X represents $R^1$ H and $R^1$ represents an alkyl group having 1 to 9 carbon atoms).

7 Claims, No Drawings

PHTHALONITRILE DERIVATIVES AND A LIQUID CRYSTAL COMPOSITION CONTAINING THE SAME

FIELD OF THE INVENTION

The present invention relates to novel phthalonitrile derivatives having large negative dielectric anisotropy and a liquid crystal composition containing the same.

BACKGROUND OF THE INVENTION

Liquid crystals having negative dielectric anisotropy are not only useful for positive type displays of guest-host type liquid crystal display devices wherein the orientation direction of liquid crystal molecules is changed by adding a dichroic dye to form a color by variation of the direction of dye molecules, but also important as materials for various liquid crystal displays such as a DSM type (dynamic scattering mode type) liquid crystal display divice utilizing a phenomenon that the liquid crystal phase causes dynamic scattering by application of a voltage or the so-called DAP type display device for carrying out pleochroic display by a polarizing plate wherein double refraction of liquid crystal is utilized by controlling an inclination of the liquid crystal.

In liquid crystal substances used in the above described display devices, various physical properties are required to have a suitable value, respectively. For example, they are stable to light or heat, they show a nematic liquid crystal phase in a wide temperature range including a room temperature, and they have large negative dielectric anisotropy, etc. However, under existing circumstances, since it is impossible to satisfy all the above described requirements for physical properties by one compound, a composition composed of several compounds is used for attaining the object.

As a result of carrying out studies for obtaining excellent liquid crystal substances in view of the above described circumstances, the present inventors have attained the present invention. An object of the present invention is to provide liquid crystal substances having large negative dielectric anisotropy.

SUMMARY OF THE INVENTION

Namely, the present inventors have sought novel phthalonitrile derivatives having two adjacent nitrile groups in the same side to the molecule axis and have found phthalonitrile derivatives represented by the formula (I) which have a large value of dielectric anisotropy:

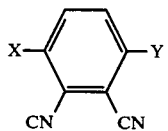
(I)

(wherein X and Y each represents an alkyl group having 1 to 9 carbon atoms, an alkoxy group having 1 to 9 carbon atoms,

-continued

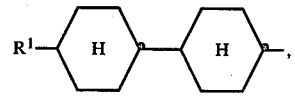

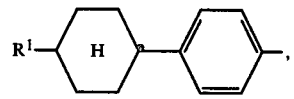

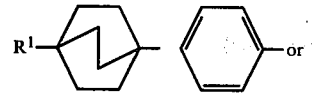

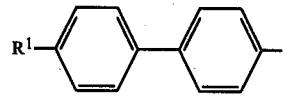

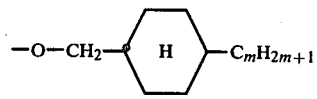

(wherein $R^1$ represents a hydrogen atom, $-C_mH_{2m+1}$, $-O-(CH_2CH_2O)_n-C_mH_{2m+1}$,

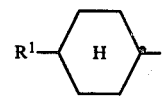

or a halogen atom, wherein m represents an integer of 1 to 9 and n represents 0, 1 or 2), but at least one of X and Y does not represent a methyl group, and Y does not represent an alkyl group having 1 to 9 carbon atoms or an alkoxy group having 1 to 9 carbon atoms in the case that X represents

[structure]

and $R^1$ represents an alkyl group having 1 to 9 carbon atoms). Thus the present invention has been attained.

DETAILED DESCRIPTION OF THE INVENTION

In the following, the present invention is illustrated. The phthalonitrile derivatives represented by the above described formula (I) of the present invention have a large negative dielectric anisotropy reaching about $-20$ in case of fusing in a liquid crystal state. Further, the novel phthalonitrile derivatives according to the present invention can be used as a mixture with known liquid crystals. As known liquid crystals, there are Schiff type liquid crystal compounds such as methoxybenzylidene butylaniline or ethoxybenzylidenebutylaniline, etc., ester type liquid crystal compounds such as p-methoxy-benzoic acid p'-pentylphenyl ester or trans-4-n-pentylcyclohexanecarboxylic acid p'-ethoxyphenyl ester, etc., azoxybenzene type liquid crystal compounds such as p-methoxy-p'-butylazoxybenzene or p-methoxy-p'-ethylazoxybenzene, etc., and oligo-1,4-phenylene type liquid crystal compounds such as 1,4-bis(trans-4-n-pentylcyclohexyl)benzene or 4-(trans-4-n-pentylcyclohexyl)biphenyl, etc.

As novel phthalonitrile derivatives represented by the formula (I), there are compounds represented by the following formulas (II) and (II').

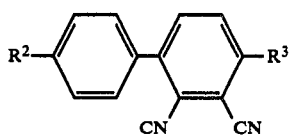 (II)

(wherein $R^2$ represents a hydrogen atom, an alkyl group having 1 to 9 carbon atoms, an alkoxy group having 1 to 9 carbon atoms, a halogen atom,

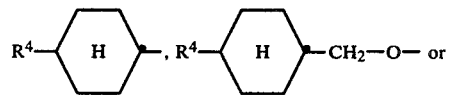

and $R^3$ represents an alkyl group having 1 to 9 carbon atoms or

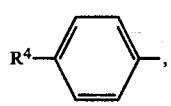

(wherein $R^4$ represents a hydrogen atom, an alkyl group having 1 to 9 carbon atoms or an alkoxy group having 1 to 9 carbon atoms)).

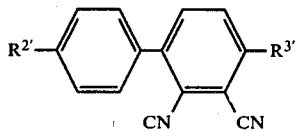 (II')

(wherein $R^{2\prime}$ represents an alkyl group having 1 to 9 carbon atoms or an alkoxy group having 1 to 9 carbon atoms, and $R^{3\prime}$ represents an alkyl group having 1 to 9 carbon atoms or

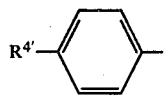

(wherein $R^{4\prime}$ represents an alkyl group having 1 to 9 carbon atoms or an alkoxy group having 1 to 9 carbon atoms)).

In case that $R^2$ represents an alkyl group having 1 to 7 carbon atoms or an alkoxy group having 1 to 7 carbon atoms and $R^3$ represents an alkyl group having 1 to 7 carbon atoms, the compounds themselves are non-liquid crystal substances. However, when they are used as a liquid crystal composition, they show a low effect of increasing viscosity and produce a good result in various characteristics such as responce speed, etc.

Further, as novel phthalonitrile derivatives represented by the formula (I), there are compounds represented by the following formulas (III) and (III').

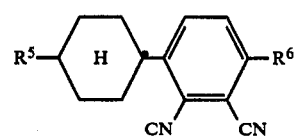 (III)

(wherein $R^5$ represents a hydrogen atom, an alkyl group having 1 to 9 carbon atoms, an alkoxy group having 1 to 9 carbon atoms or

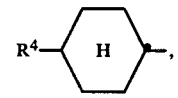, and $R^6$ represents an alkyl group having 1 to 9 carbon atoms, an alkoxy group having 1 to 9 carbon atoms,

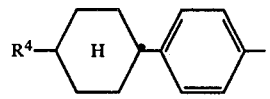 or

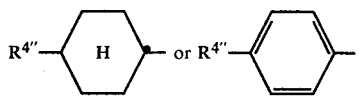

(wherein $R^4$ represents a halogen atom, a hydrogen atom, an alkyl group having 1 to 9 carbon atoms or an alkoxy group having 1 to 9 carbon atoms), but $R^6$ does not represent an alkyl group having 1 to 9 carbon atoms or an alkoxy group having 1 to 9 carbon atoms in the case that $R^5$ represents an alkyl group having 1 to 9 carbon atoms).

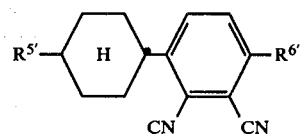 (III')

(wherein $R^{5\prime}$ represents a hydrogen atom, an alkyl group having 1 to 9 carbon atoms or an alkoxy group having 1 to 9 carbon atoms, and $R^{6\prime}$ represents

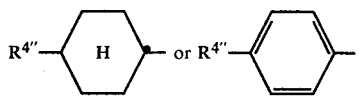

(wherein $R^{4\prime\prime}$ represents a halogen atom, an alkyl group having 1 to 9 carbon atoms or an alkoxy group having 1 to 9 carbon atoms).

In case that $R^5$ represents an alkyl group having 1 to 7 carbon atoms and $R^6$ represents

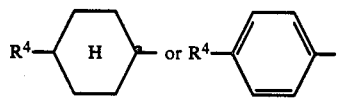

(wherein $R^4$ represents an alkyl group having 1-7 carbon atoms or an alkoxy group having 1 to 7 carbon atoms), the compounds easily have a liquid crystal characteristic. When they are used as a liquid crystal composition, they have a wide range of liquid crystal temperature as compared with the case of using compounds in which $R^6$ represents an alkyl group or an alkoxy group, and they exhibit an excellent effect in responce characteristics.

Moreover, as novel phthalonitrile derivatives represented by the formula (I), there are compounds represented by the following formula (IV).

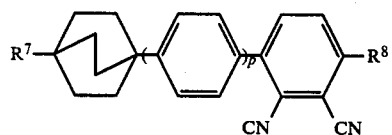

(wherein $R^7$ represents an alkyl group having 1 to 9 carbon atoms, $R^8$ represents an alkyl group having 1 to 9 carbon atoms, an alkoxy group having 1 to 9 carbon atoms,

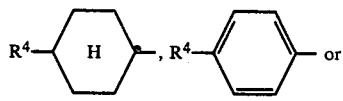

(wherein $R^4$ represents a hydrogen atom, an alkyl group having 1 to 9 carbon atoms or an alkoxy group having 1 to 9 carbon atoms), and p represents 0 or 1). These compounds are similarly useful as liquid crystal materials for guest-host type positive display. In case of using compounds wherein $R^7$ represents an alkyl group having 1 to 7 carbon atoms, p is 0 and $R^8$ represents

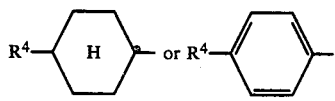

(wherein $R^4$ represents an alkyl group having 1 to 7 carbon atoms or an alkoxy group having 1 to 7 carbon atoms), it is possible to obtain a liquid crystal composition which shows a small temperature dependence of threshold voltage.

These compounds represented by the formulas (II), (III) and (IV) can be used as a mixture with known liquid crystals as described in the case of the formula (I).

The novel phthalonitrile derivatives represented by the formula (I) are synthesized by, for example, the following process for production.

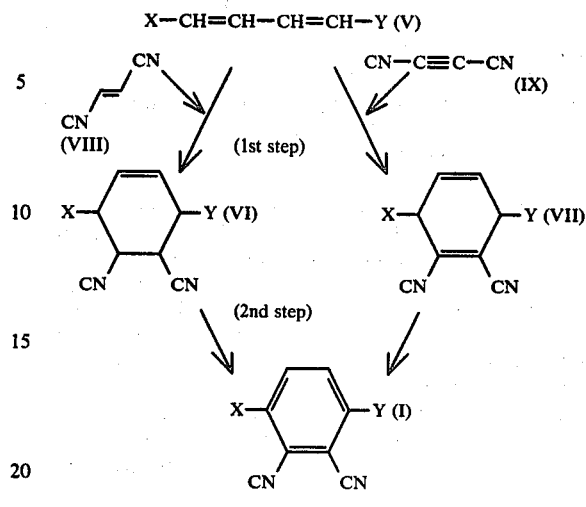

(The 1st step)

A butadiene derivative represented by the formula (V) and fumaronitrile (VI) or dicyanoacetylene (IX) are subjected to cyclization reaction to produce a 1,2,3,6-tetrahydrophthalonitrile derivative represented by the formula (VI) and a 3,6-dihydrophthalonitrile derivative represented by the general formula (VII), respectively. The reaction is carried out in an absence of solvents or in a solvent such as benzene, toluene, xylene, chlorobenzene or dichlorobenzene, etc. at a reaction temperature of 10°–250° C. with adding, if necessary, a catalyst such as hydroquinone.

(The 2nd step)

The 1,2,3,6-tetrahydrophthalonitrile derivative represented by the formula (VI) or the 3,6-dihydrophthalonitrile derivative represented by the formula (VII) is oxidized by sulfur in an absence of solvents or in a solvent such as N,N-dimethylformamide or N-methylpyrrolidone, etc., or brominated in a solvent such as acetic acid and, thereafter, carrying out dehydrobromination to produce a novel phthalonitrile derivative represented by the formula (I).

Hitherto, as phthalonitrile compounds having a negative dielectric constant, 3-alkyloxy-6-cyclohexanecarboxy-phthalonitrile (Japanese Patent Application (OPI) No. 102550/80 and 3-alkyl-6-alkylcyclohexyl-phthalonitrile (DE No. 2,933,563) have been known. The phthalonitrile derivatives of the present invention are practically very useful, because the responce speed is greatly improved in case of using them for, for example, guest-host type liquid crystal display because of having a lower viscosity than the above described known compounds (the former), and they show a wide liquid crystal temperature range as compared with the above described known compounds (the latter).

Further, the phthalonitrile compounds of the present invention are useful as liquid crystal materials for TN liquid crystal display and, particularly, liquid crystal materials for carrying out high time split driving in addition to the above described materials for Guest-host type liquid crystal display.

For example, in order to carry out time split driving, it is important to have a good rising characteristic of luminance brightness in case of applying a voltage to the liquid crystal device. In order to increase a time split drive ratio (number of scanning lines), it is necessary to improve the rising characteristic. This rising characteristic is concerned with the dielectric parameter ($\Delta\epsilon/\epsilon\perp$) of the liquid crystal material, and a case having a lower value of $\Delta\epsilon/\epsilon\perp$ is preferable (Japanese Patent Application (OPI) No. 16087/82).

In case of using the prior phthalonitrile compounds, it is difficult to reduce the value of $\Delta\epsilon/\epsilon\perp$ to 2 or less. Even if the value of $\Delta\epsilon/\epsilon\perp$ can be reduced, it is not preferred, because the viscosity increases.

On the contrary, when the value $\Delta\epsilon/\epsilon\perp$ and the viscosity of liquid crystal materials for TN which are produced using the phthalonitrile compounds of the present invention are examined, it is understood that a composition having a value of $\Delta\epsilon/\epsilon\perp$ of 1.5 or less can be obtained without changing the viscosity, and the time split drive ratio can be increased twice or more times as compared with the prior cases.

In the following, the present invention is illustrated in greater detail with reference to examples, but it is not limited to examples unless it departs from the gist of the present invention.

In the following examples, m.p. means a melting point and cl.p. means a phase transition point.

EXAMPLE 1

1.0 g of 1,4-bis-(p-n-butoxyphenyl)-1,3-butadiene and 0.3 g of fumaronitrile were blended and subjected to reacting at 170°–180° C. in a nitrogen stream for 7 hours. After cooled, separation was carried out by column chromatography using silica gel as a carrier and chloroform as a separation solvent to obtain 1.1 g of a crude product of 3,6-bis-(p-n-butoxyphenyl)-1,2,3,6-tetrahydrophthalonitrile. $M^+(m/e)=428$ was shown in mass spectrum.

0.3 g of the resulted crude product and 0.05 g of sulfur were added to 20 ml of N-methylpyrrolidone, and the mixture was refluxed with heating for 2 hours. After cooled, N-methylpyrrolidone was distilled away under a reduced pressure, and the residue was purified by column chromatography using silica gel as a carrier and chloroform-n-hexane (2:1) as a separation solvent to obtain 0.07 g of 3,7-bis-(p-n-butoxyphenyl)phthalonitrile. m.p. was 179.5° C.

Likewise, the following compounds were obtained.
3,6-Bis-(p-n-propyloxyphenyl)phthalonitrile.
3,6-Bis-(p-n-pentyloxyphenyl)phthalonitrile.
3,6-Bis-(p-n-heptyloxyphenyl)phthalonitrile.
3,6-Bis-(p-n-octyloxyphenyl)phthalonitrile.

EXAMPLE 2

2.6 g of 1-(p-methoxyphenyl)-4-(p'-n-heptyloxyphenyl)-1,3-butadiene and 0.73 g of dicyanoacetylene were blended and subjected to reacting in a sealed tube at 120° C. for 5 hours. After cooled, separation was carried out by column chromatography using silica gel as a carrier and chloroform as a separation solvent to obtain 2.5 g of a crude product of 3-(p-methoxyphenyl)-6-(p'-n-heptyloxyphenyl)-3,6-dihydrophthalonitrile. $M^+(m/e)=426$ was shown in mass spectrum.

2.0 g of the crude product and 1.2 g of sodium acetate were added to 20 ml of acetic acid, and 0.75 g of bromine was slowly added dropwise thereto with heating to 110° C. The reaction was carried out at this temperature for 2 hours. After cooled, water was added and extraction was carried out with chloroform. After chloroform was distilled away under a reduced pressure, the residue was purified by column chromatography using n-hexane (2:1) as a separation solvent to obtain 0.6 g of 3-(p-methoxyphenyl)-6-(p'-n-heptyloxyphenyl)phthalonitrile. It was a monotropic nematic liquid crystal having m.p. of 125.5° C. and cl.p. of 120° C.

Likewise, the following compounds were obtained.
3-(p-Methoxyphenyl)-6-(p'-ethoxyphenyl)phthalonitrile.
3-(p-Methoxyphenyl)-6-(p'-n-propyloxyphenyl)phthalonitrile.
3-(p-Methoxyphenyl)-6-(p'-n-butoxyphenyl)phthalonitrile.
3-(p-Methoxyphenyl)-5-(p'-n-hexyloxyphenyl)phthalonitrile.
3-(p-Ethoxyphenyl)-6-(p'-n-ethoxyphenyl)phthalonitrile.
3-(p-Ethoxyphenyl)-6-(p'-n-propyloxyphenyl)phthalonitrile.
3-(p-Ethoxyphenyl)-6-(p'-n-butoxyphenyl)phthalonitrile.
3-(p-Ethoxyphenyl)-6-(p'-n-pentyloxyphenyl)phthalonitrile.
3-(p-Ethoxyphenyl)-6-(p'-n-hexyloxyphenyl)phthalonitrile.
3-(p-Ethoxyphenyl)-6-(p'-n-heptyloxyphenyl)phthalonitrile.
3-(p-n-Propyloxyphenyl)-6-(p'-n-propyloxyphenyl)phthalonitrile.
3-(p-n-Propyloxyphenyl)-6-(p'-n-butoxyphenyl)phthalonitrile.
3-(p-n-Butoxyphenyl)-6-(p'-n-butoxyphenyl)phthalonitrile.
3-(p-n-Butoxyphenyl)-6-(p'-n-pentyloxyphenyl)phthalonitrile.
3-(p-n-Butoxyphenyl)-6-(p'-hexyloxyphenyl)phthalonitrile.
3-(p-n-Pentyloxyphenyl)-6-(p'-n-methoxyphenyl)phthalonitrile.
3-(p-n-Pentyloxyphenyl)-6-(p'-n-propyloxyphenyl)phthalonitrile.
3-(p-n-Pentyloxyphenyl)-6-(p'-n-pentyloxyphenyl)phthalonitrile.
3-(p-n-Pentyloxyphenyl)-6-(p'-n-hexyloxyphenyl)phthalonitrile.

EXAMPLE 3

Using 1-(p-n-butoxyphenyl)-4-(p'-n-pentylphenyl)-1,3-butadiene and fumaronitrile, 3-(p-n-butoxyphenyl)-6-(p'-n-pentylphenyl)phthalonitrile was obtained by the same method as in Example 1. m.p. was 159° C.

Likewise, the following compounds were obtained.
3-(p-n-Propylphenyl)-6-(p'-ethoxyphenyl)phthalonitrile.
3-(p-n-Propylphenyl)-6-(p'-n-propyloxyphenyl)phthalonitrile.
3-(p-n-Propylphenyl)-6-(p'-n-butoxyphenyl)phthalonitrile.
3-(p-n-Propylphenyl)-6-(p'-n-pentyloxyphenyl)phthalonitrile.
3-(p-n-Pentylphenyl)-6-(p'-ethoxyphenyl)phthalonitrile.
3-(p-n-Pentylphenyl)-6-(p'-n-propyloxyphenyl)phthalonitrile.
3-(p-n-Pentylphenyl)-6-(p'-n-butoxyphenyl)phthalonitrile.
3-(p-n-Pentylphenyl)-6-(p'-n-pentyloxyphenyl)phthalonitrile.
3-(p-n-Pentylphenyl)-6-(p'-n-hexyloxyphenyl)phthalonitrile.

3-(p-n-Pentylphenyl)-6-(p'-n-heptyloxyphenyl)phthalonitrile.
3-(p-n-Hexylphenyl)-6-(p'-methoxyphenyl)phthalonitrile.
3-(p-n-Hexylphenyl)-6-(p'-ethoxyphenyl)phthalonitrile.
3-(p-n-Hexylphenyl)-6-(p'-n-propyloxyphenyl)phthalonitrile.
3-(p-n-Hexylphenyl)-6-(p'-n-Butoxyphenyl)phthalonitrile.
3-(p-n-Heptylphenyl)-6-(p'-n-methoxyphenyl)phthalonitrile.
3-(p-n-Heptylphenyl)-6-(p'-n-propyloxyphenyl)phthalonitrile.
3-(p-n-Octylphenyl)-6-(p'-methoxyphenyl)phthalonitrile.
3-(p-n-Octylphenyl)-6-(p'-ethoxyphenyl)phthalonitrile.
3-(p-Octyloxyphenyl)-6-(p'-n-propyloxyphenyl)phthalonitrile.

EXAMPLE 4

Using 1-(p-n-butoxyphenyl)-4-methyl-1,3-butadiene and fumaronitrile, 3-(p-n-butoxyphenyl)-6-methylphthalonitrile was obtained by the same method as in Example 1. m.p. was 151.5° C.

Likewise, the following compounds were obtained.
3-(p-Methoxyphenyl)-6-n-propylphthalonitrile.
3-(p-Methoxyphenyl)-6-n-butylphthalonitrile.
3-(p-Methoxyphenyl)-6-n-pentylphthalonitrile.
3-(p-Methoxyphenyl)-6-n-hexylphthalonitrile.
3-(p-Methoxyphenyl)-6-n-heptylphthalonitrile.
3-(p-Ethoxyphenyl)-6-n-propylphthalonitrile.
3-(p-Ethoxyphenyl)-6-n-butylphthalonitrile.
3-(p-Ethoxyphenyl)-6-n-pentylphthalonitrile.
3-(p-Ethoxyphenyl)-6-n-hexylphthalonitrile.
3-(p-Ethoxyphenyl)-6-n-heptylphthalonitrile.
3-(p-Ethoxyphenyl)-6-n-octylphthalonitrile.
3-(p-Ethoxyphenyl)-6-n-nonylphthalonitrile.
3-(p-n-Propyloxyphenyl)-6-n-propylphthalonitrile.
3-(p-n-Propyloxyphenyl)-6-n-butylphthalonitrile.
3-(p-n-Propyloxyphenyl)-6-n-pentylphthalonitrile.
3-(p-n-Propyloxyphenyl)-6-n-hexylphthalonitrile.
3-(p-Propyloxyphenyl)-6-n-heptylphthalonitrile.
3-(p-n-Butoxyphenyl)-6-ethylphthalonitrile.
3-(p-n-Butoxyphenyl)-6-n-propylphthalonitrile.
3-(p-n-Butoxyphenyl)-6-n-butylphthalonitrile.
3-(p-n-Butoxyphenyl)-6-n-pentylphthalonitrile.
3-(p-n-Butoxyphenyl)-6-n-hexylphthalonitrile.
3-(p-n-Pentyloxyphenyl)-6-methylphthalonitrile.
3-(p-n-Pentyloxyphenyl)-6-ethylphthalonitrile.
3-(p-n-Pentyloxyphenyl)-6-n-propylphthalonitrile.
3-(p-n-Pentyloxyphenyl)-6-n-butylphthalonitrile.
3-(p-n-Pentyloxyphenyl)-6-n-pentylphthalonitrile.
3-(p-n-Pentyloxyphenyl)-6-n-hexylphthalonitrile.
3-(p-n-Pentyloxyphenyl)-6-n-heptylphthalonitrile.
3-(p-n-Hexyloxyphenyl)-6-n-propylphthalonitrile.
3-(p-n-Hexyloxyphenyl)-6-n-butylphthalonitrile.
3-(p-n-Hexyloxyphenyl)-6-n-pentylphthalonitrile.
3-(p-n-Heptyloxyphenyl)-6-n-propylphthalonitrile.
3-(p-n-Heptyloxyphenyl)-6-n-butylphthalonitrile.
3-(p-n-Heptyloxyphenyl)-6-n-pentylphthalonitrile.
3-(p-(Trans-4'-n-propylcyclohexylmethoxy)phenyl)-6-n-pentylphthalonitrile.
3-(p-(Trans-4'-n-pentylcyclohexylmethoxy)phenyl)-6-n-propylphthalonitrile.

EXAMPLE 5

Using 1-(Trans-4'-n-propylcyclohexyl)-4-(p-n-butoxyphenyl)-1,3-butadiene and fumaronitrile, 3-(trans-4'-n-propylcyclohexyl)-6-(p-n-butoxyphenyl)phthalonitrile was obtained by the same method as in Example 1. m.p. was 115° C.

Likewise, the following compounds were obtained.
3-(Trans-4'-n-propylcyclohexyl)-6-(p-methoxyphenyl)phthalonitrile.
3-(Trans-4'-n-propylcyclohexyl)-6-(p-ethoxyphenyl)phthalonitrile.
3-(Trans-4'-n-propylcyclohexyl)-6-(p-n-propyloxyphenyl)phthalonitrile.
3-(Trans-4'-n-propylcyclohexyl)-6-(p-n-pentyloxyphenyl)phthalonitrile.
3-(Trans-4'-n-propylcyclohexyl)-6-(p-n-hexyloxyphenyl)phthalonitrile.
3-(Trans-4'-n-propylcyclohexyl)-6-(p-n-heptyloxyphenyl)phthalonitrile.
3-(Trans-4'-n-butylcyclohexyl)-6-(p-methoxyphenyl)phthalonitrile.
3-(Trans-4'-n-butylcyclohexyl)-6-(p-ethoxyphenyl)phthalonitrile.
3-(Trans-4'-n-butylcyclohexyl)-6-(p-n-propyloxyphenyl)phthalonitrile.
3-(Trans-4'-n-butylcyclohexyl)-6-(p-n-butoxyphenyl)phthalonitrile.
3-(Trans-4'-n-butylcyclohexyl)-6-(p-n-pentyloxyphenyl)phthalonitrile.
3-(Trans-4'-n-butylcyclohexyl)-6-(p-n-hexyloxyphenyl)phthalonitrile.
3-(Trans-4'-n-butylcyclohexyl)-6-(p-n-heptyloxyphenyl)phthalonitrile.
3-(Trans-4'-n-pentylcyclohexyl)-6-(p-methoxyphenyl)phthalonitrile.
3-(Trans-4'-n-pentylcyclohexyl)-6-(p-ethoxyphenyl)phthalonitrile.
3-(Trans-4'-n-pentylcyclohexyl)-6-(p-n-propyloxyphenyl)phthalonitrile.
3-(Trans-4'-n-pentylcyclohexyl)-6-(p-n-butoxyphenyl)phthalonitrile.
3-(Trans-4'-n-pentylcyclohexyl)-6-(p-n-pentyloxyphenyl)phthalonitrile.
3-(Trans-4'-n-pentylcyclohexyl)-6-(p-n-hexyloxyphenyl)phthalonitrile.
3-(Trans-4'-n-pentylcyclohexyl)-6-(p-n-heptyloxyphenyl)phthalonitrile.
3-(Trans-4'-n-hexylcyclohexyl)-6-(p-methoxyphenyl)phthalonitrile.
3-(Trans-4'-n-hexylcyclohexyl)-6-(p-ethoxyphenyl)phthalonitrile.
3-(Trans-4'-n-hexylcyclohexyl)-6-(p-n-propyloxyphenyl)phthalonitrile.
3-(Trans-4'-n-hexylcyclohexyl)-6-(p-n-butoxyphenyl)phthalonitrile.
3-(Trans-4'-n-hexylcyclohexyl)-6-(p-n-pentyloxyphenyl)phthalonitrile.
3-(Trans-4'-n-hexylcyclohexyl)-6-(p-n-hexyloxyphenyl)phthalonitrile.
3-(Trans-4'-n-hexylcyclohexyl)-6-(p-n-heptyloxyphenyl)phthalonitrile.
3-(Trans-4'-n-heptylcyclohexyl)-6-(p-methoxyphenyl)phthalonitrile.
3-(Trans-4'-n-heptylcyclohexyl)-6-(p-ethoxyphenyl)phthalonitrile.
3-(Trans-4'-n-heptylcyclohexyl)-6-(p-n-propyloxyphenyl)phthalonitrile.
3-(Trans-4'-n-heptylcyclohexyl)-6-(p-n-butoxyphenyl)phthalonitrile.
3-(Trans-4'-n-heptylcyclohexyl)-6-(p-n-pentyloxyphenyl)phthalonitrile.

3-(Trans-4'-n-heptylcyclohexyl)-6-(p-n-hexyloxyphenyl)phthalonitrile.
3-(Trans-4'-n-heptylcyclohexyl)-6-(p-n-heptyloxyphenyl)phthalonitrile.
3-(Trans-4'-n-propylcyclohexyl)-6-(p-(trans-4'-n-pentylcyclohexylmethoxy)phenyl)phthalonitrile.

EXAMPLE 6

Using 1-(trans-4'-n-propylcyclohexyl)-4-(p-n-pentylphenyl)-1,3-butadiene and fumaronitrile, 3-(trans-4'-n-propylcyclohexyl)-6-(p-n-pentylphenyl)phthalonitrile was obtained by the same method as in Example 1. m.p. was 97° C.

Likewise, the following compounds were obtained.
3-(Trans-4'-n-propylcyclohexyl)-6-p-tolyl-phthalonitrile.
3-(Trans-4'-n-propylcyclohexyl)-6-(p-ethylphenyl)phthalonitrile.
3-(Trans-4'-n-propylcyclohexyl)-6-(p-n-propylphenyl)phthalonitrile.
3-(Trans-4'-n-propylcyclohexyl)-6-(p-n-butylphenyl)phthalonitrile.
3-(Trans-4'-n-propylcyclohexyl)-6-(p-n-hexylphenyl)phthalonitrile.
3-(Trans-4'-n-propylcyclohexyl)-6-(p-n-heptylphenyl)phthalonitrile.
3-(Trans-4'-n-butylcyclohexyl)-6-p-tolyl-phthalonitrile.
3-(Trans-4'-n-propylcyclohexyl)-6-(p-n-heptylphenyl)phthalonitrile.
3-(Trans-4'-n-butylcyclohexyl)-6-p-tolyl-phthalonitrile.
3-(Trans-4'-n-butylcyclohexyl)-6-(p-ethylphenyl)phthalonitrile.
3-(Trans-4'-n-butylcyclohexyl)-6-(p-n-propylphenyl)phthalonitrile.
3-(Trans-4'-n-butylcyclohexyl)-6-(p-b-butylphenyl)phthalonitrile.
3-(Trans-4'-n-butylcyclohexyl)-6-(p-n-pentylphenyl)phthalonitrile.
3-(Trans-4'-n-butylcyclohexyl)-6-(p-n-hexylphenyl)phthalonitrile.
3-(Trans-4'-n-butylcyclohexyl)-6-(p-n-heptylphenyl)phthalonitrile.
3-(Trans-4'-n-pentylcyclohexyl)-6-p-tolyl-phthalonitrile.
3-(Trans-4'-n-pentylcyclohexyl)-6-(p-ethylphenyl)phthalonitrile.
3-(Trans-4'-n-pentylcyclohexyl)-6-(p-n-propylphenyl)phthalonitrile.
3-(Trans-4'-n-pentylcyclohexyl)-6-(p-n-butylphenyl)phthalonitrile.
3-(Trans-4'-n-pentylcyclohexyl)-6-(p-n-pentylphenyl)phthalonitrile.
3-(Trans-4'-n-pentylcyclohexyl)-6-(p-n-hexylphenyl)phthalonitrile.
3-(Trans-4'-n-pentylcyclohexyl)-6-(p-n-heptylphenyl)phthalonitrile.
3-(Trans-4'-n-hexylcyclohexyl)-6-p-tolyl-phthalonitrile.
3-(Trans-4'-n-hexylcyclohexyl)-6-(p-ethylphenyl)phthalonitrile.
3-(Trans-4'-n-hexylcyclohexyl)-6-(p-n-propylphenyl)phthalonitrile.
3-(Trans-4'-n-hexylcyclohexyl)-6-(p-n-butylphenyl)phthalonitrile.
3-(Trans-4'-n-hexylcyclohexyl)-6-(p-n-pentylphenyl)phthalonitrile.
3-(Trans-4'-n-hexylcyclohexyl)-6-(p-n-hexylphenyl)phthalonitrile.
3-(Trans-4'-n-hexylcyclohexyl)-6-(p-n-heptylphenyl)phthalonitrile.
3-(Trans-4'-n-heptylcyclohexyl)-6-p-tolyl-phthalonitrile.
3-(Trans-4'-n-heptylcyclohexyl)-6-(p-ethylphenyl)phthalonitrile.
3-(Trans-4'-n-heptylcyclohexyl)-6-(p-n-propylphenyl)phthalonitrile.
3-(Trans-4'-n-heptylcyclohexyl)-6-(p-n-butylphenyl)phthalonitrile.
3-(Trans-4'-n-heptylcyclohexyl)-6-(p-n-pentylphenyl)phthalonitrile.
3-(Trans-4'-n-heptylcyclohexyl)-6-(p-n-hexylphenyl)phthalonitrile.
3-(Trans-4'-n-heptylcyclohexyl)-6-(p-n-heptylphenyl)phthalonitrile.

EXAMPLE 7

Using 1-(p-n-butoxyphenyl)-6-(p'-(trans-4'-n-pentylcyclohexyl)phenyl)-1,3-butadiene and fumaronitrile, 3-(p-n-butoxy)-6-(p'-(trans-4'-n-pentylcyclohexyl)phenyl)phthalonitrile was obtained by the same method as in Example 1. m.p. was 175° C. and cl.p. was 264° C.

Likewise, the following compounds were obtained.
3-(p-n-Methoxyphenyl)-6-(p'-(trans-4'-n-propylcyclohexyl)phenyl)phthalonitrile.
3-(p-Methoxyphenyl)-6-(p'-(trans-4'-n-pentylcyclohexyl)phenyl)phthalonitrile.
3-(p-Methoxyphenyl)-6-(p'-(trans-4'-n-heptylcyclohexyl)phenyl)phthalonitrile.
3-(p-Ethoxyphenyl)-6-(p'-(trans-4'-n-propylcyclohexyl)phenyl)phthalonitrile.
3-(p-Ethoxyphenyl)-6-(p'-(trans-4'-n-pentylcyclohexyl)phenyl)phthalonitrile.
3-(p-Ethoxyphenyl)-6-(p'-(trans-4'-n-heptylcyclohexyl)phenyl)phthalonitrile.
3-(p-n-Propyloxyphenyl)-6-(p'-(trans-4'-n-propylcyclohexyl)phenyl)phthalonitrile.
3-(p-n-Propyloxyphenyl)-6-(p'-(trans-4'-n-pentylcyclohexyl)phenyl)phthalonitrile.
3-(p-n-Propyloxyphenyl)-6-(p'-(trans-4'-n-heptylcyclohexyl)phenyl)phthalonitrile.
3-(p-n-Butoxyphenyl)-6-(p'-(trans-4'-n-propylcyclohexyl)phenyl)phthalonitrile.
3-(p-n-Pentyloxyphenyl)-6-(p'-(trans-4'-n-propylcyclohexyl)phenyl)phthalonitrile.
3-(p-n-pentyloxyphenyl)-6-(p'-(trans-4'-n-pentylcyclohexyl)phenyl)phthalonitrile.
3-(p-n-Hexyloxyphenyl)-6-(p'-(trans-4'-n-propylcyclohexyl)phenyl)phthalonitrile.
3-(p-n-Heptyloxyphenyl)-6-(p'-(trans-4'-n-propylcyclohexyl)phenyl)phthalonitrile.

EXAMPLE 8

Using 1-(p-fluorophenyl)-4-(trans-4'-n-pentylcyclohexyl)-1,3-butadiene and fumaronitrile, 3-(p-fluorophenyl)-6-(trans-4'-n-pentylcyclohexyl)phthalonitrile was obtained by the same method as in Example 1. m.p. was 102.5° C.

Likewise, the following compounds were obtained.
3-(p-Fluorophenyl)-6-(trans-4'-n-propylcyclohexyl)phthalonitrile.
3-(p-Fluorophenyl)-6-(trans-4'-n-butylcyclohexyl)phthalonitrile.
3-(p-Fluorophenyl)-6-(trans-4'-n-hexylcyclohexyl)phthalonitrile.
3-(p-Fluorophenyl)-6-(trans-4'-n-heptylcyclohexyl)phthalonitrile.

EXAMPLE 9

Using 1-cyclohexyl-4-(trans-4'-n-propylcyclohexyl)-1,3-butadiene and fumaronitrile, 3-cyclohexyl-6-(trans-4'-n-propylcyclohexyl)phthalonitrile was obtained by the same method as in Example 1. It was a monotropic nematic liquid crystal having m.p. of 102.5° C. and cl.p. of 92° C.

Likewise, the following compounds were obtained.
3-Cyclohexyl-6-(trans-4'-n-butylcyclohexyl)phthalonitrile.
3-Cyclohexyl-6-(trans-4'-n-pentylcyclohexyl)phthalonitrile.
3-Cyclohexyl-6-(trans-4'-n-hexylcyclohexyl)phthalonitrile.
3-Cyclohexyl-6-(trans-4'-n-heptylcyclohexyl)phthalonitrile.
3-(Trans-4'-n-propylcyclohexyl)-6-(trans-4'-n-butylcyclohexyl)phthalonitrile.
3-(Trans-4'-n-propylcyclohexyl)-6-(trans-4''-n-hexylcyclohexyl)phthalonitrile.
3-(Trans-4'-n-propylcyclohexyl)-6-(trans-4''-n-heptylcyclohexyl)phthalonitrile.
3-(Trans-4'-propylcyclohexyl)-6-(trans-4''-n-octylcyclohexyl)phthalonitrile.
3-(Trans-4'-n-butylcyclohexyl)-6-(trans-4''-n-butylcyclohexyl)phthalonitrile.
3-(Trans-4'-n-butylcyclohexyl)-6-(trans-4''-n-pentylcyclohexyl)phthalonitrile.
3-(Trans-4'-n-butylcyclohexyl)-6-(trans-4''-n-hexylcyclohexyl)phthalonitrile.
3-(Trans-4'-n-butylcyclohexyl)-6-(trans-4''-n-heptylcyclohexyl)phthalonitrile.
3-(Trans-4'-n-pentylcyclohexyl)-6-(trans-4''-n-pentylcyclohexyl)phthalonitrile.
3-(Trans-4'-n-pentylcyclohexyl)-6-(trans-4''-n-hexylcyclohexyl)phthalonitrile.

EXAMPLE 10

Using 1-(p-(trans-4'-n-pentylcyclohexyl)phenyl)-4-(trans-4''-n-pentylcyclohexyl)-1,3-butadiene and fumaronitrile, 3-(p-(trans-4'-n-pentylcyclohexyl)phenyl)-6-(trans-4'-n-pentylcyclohexyl)phthalonitrile was obtained by the same method as in Example 1.

Likewise, the following compounds were obtained.
3-(p-(Trans-4'-n-propylcyclohexyl)phenyl)-6-(trans-4''-n-propylcyclohexyl)phthalonitrile.
3-(p-Trans-4'-n-propylcyclohexyl)phenyl)-6-(trans-4''-n-butylcyclohexyl)phthalonitrile.
3-(p-(Trans-4'-n-propylcyclohexyl)phenyl)-6-(trans-4''-n-pentylcyclohexyl)phthalonitrile.
3-(p-(Trans-4'-n-propylcyclohexyl)phenyl)-6-trans-4''-n-hexylcyclohexyl)phthalonitrile.
3-(p-(Trans-4'-n-propylcyclohexyl)phenyl)-6-(trans-4''-n-heptylcyclohexyl)phthalonitrile.
3-(p-(Trans-4'-n-pentylcyclohexyl)phenyl)-6-(trans-4''-n-butylcyclohexxyl)phthalonitrile.
3-(p-(Trans-4'-n-pentylcyclohexyl)phenyl)-6-(trans-4''-n-propylcyclohexyl)phthalonitrile.
3-(p-Trans-4'-n-pentylcyclohexyl)phenyl)-6-(trans-4''-n-hexylcyclohexyl)phthalonitrile.
3-(p-(Trans-4'-n-heptylcyclohexyl)phenyl)-6-(trans-4''-n-propylcyclohexyl)phthalonitrile.
3-(p-(Trans-4'-n-heptylcyclohexyl)phenyl)-6-(trans-4''-n-butylcyclohexyl)phthalonitrile.

EXAMPLE 11

Using 1-(p-n-propylphenyl)-4-(p'-n-pentylphenyl)-1,3-butadiene and fumaronitrile, 3-(p-n-propylphenyl)-6-(p'-n-pentylphenyl)phthalonitrile was obtained by the same method as in Example 1.

Likewise, the following compounds were obtained.
3-(p-n-Propylphenyl)-6-(p'-n-butylphenyl)phthalonitrile.
3-(p-n-Propylphenyl)-6-(p'-n-hexylphenyl)phthalonitrile.
3-(p-n-Propylphenyl)-6-(p'-n-heptylphenyl)phthalonitrile.
3-(p-n-Propylphenyl)-6-(p'-n-octylphenyl)phthalonitrile.
3-(p-n-Butylphenyl)-6-(p'-n-butylphenyl)phthalonitrile.
3-(p-n-Butylphenyl)-6-(p'-n-pentylphenyl)phthalonitrile.
3-(p-n-Butylphenyl)-6-(p'-n-hexylphenyl)phthalonitrile.
3-(p-n-Butylphenyl)-6-(p'-n-heptylphenyl)phthalonitrile.
3-(p-n-Pentylphenyl)-6-(p'-n-pentylphenyl)phthalonitrile.
3-(p-n-Pentylphenyl)-6-(p'-n-hexylphenyl)phthalonitrile.

EXAMPLE 12

Using 1-(trans-trans-4'-n-propylcyclohexylcyclohexyl)-4-methyl-1,3-butadiene and fumaronitrile, 3-(trans-trans-4'-n-propylcyclohexylcyclohexyl)-6-methylphthalonitrile was obtained by the same method as in Example 1.

Likewise, the following compounds were obtained.
3-(Trans-trans-4'-n-propylcyclohexylcyclohexyl)-6-ethylphthalonitrile.
3-(Trans-trans-4'-n-propylcyclohexylcyclohexyl)-6-n-propylphthalonitrile.
3-(Trans-trans-4'-n-propylcyclohexylcyclohexyl)-6-n-butylphthalonitrile.
3-(Trans-trans-4'-n-pentylcyclohexylcyclohexyl)-6-methylphthalonitrile.
3-(Trans-trans-4'-n-pentylcyclohexylcyclohexyl)-6-ethylphthalonitrile.
3-(Trans-trans-4'-n-pentylcyclohexylcyclohexyl)-6-n-propylphthalonitrile.
3-(Trans-trans-4'-n-heptylcyclohexylcyclohexyl)-6-methylphthalonitrile.
3-(Trans-trans-4'-n-heptylcyclohexylcyclohexyl)-6-ethylphthalonitrile.
3-(Trans-trans-4'-n-heptylcyclohexylcyclohexyl)-6-n-propylphthalonitrile.

EXAMPLE 13

Using 1-(trans-4'-n-propyloxycyclohexyl)-4-(p-n-pentylphenyl)-1,3-butadiene and fumaronitrile, 3-(trans-4'-n-propyloxycyclohexyl-6-(p-n-pentylphenyl)phthalonitrile was obtained.

Likewise, the following compounds were obtained.
3-(Trans-4'-n-propyloxycyclohexyl)-6-p-tolylphthalonitrile.
3-(Trans-4'-propyloxycyclohexyl)-6-(p-ethylphenyl)phthalonitrile.
3-(Trans-4'-n-propyloxycyclohexyl)-6-(p-n-propylphenyl)phthalonitrile.
3-(Trans-4'-n-propyloxycyclohexyl)-6-(p-n-butylphenyl)phthalonitrile.
3-(Trans-4'-n-propyloxycyclohexyl)-6-(p-n-pentylphenyl)phthalonitrile.

3-(Trans-4'-n-pentyloxycyclohexyl)-6-(p-ethylphenyl)phthalonitrile.
3-(Trans-4'-n-pentyloxycyclohexyl)-6-(p-n-propylphenyl)phthalonitrile.
3-(Trans-4'-n-heptyloxycyclohexyl)-6-(p-ethylphenyl)phthalonitrile.
3-(Trans-4'-n-heptyloxycyclohexyl)-6-(p-n-propylphenyl)phthalonitrile.

EXAMPLE 14

Using 1-(p-4'-n-propyloxyphenyl)phenyl)-4-methyl-1,3-butadiene and fumaronitrile, 3-(p-(4'-n-propyloxyphenyl)phenyl)-6-methylphthalonitrile was obtained by the same method as in Example 1.

Likewise, the following compounds were obtained.
3-(p-(4'-n-Propyloxyphenyl)phenyl)-6-ethylphthalonitrile.
3-(p-(4'-n-propyloxyphenyl)phenyl)-6-n-propylphthalonitrile.
3-(p-(4'-n-Propyloxyphenyl)phenyl)-6-n-butylphthalonitrile.
3-(p-(4'-n-Propyloxyphenyl)phenyl)-6-n-pentylphthalonitrile.
3-(p-(4'-n-Pentyloxyphenyl)phenyl)-6-ethylphthalonitrile.
3-(p-(4'-n-Pentyloxyphenyl)phenyl)-6-n-propylphthalonitrile.
3-(p-(4'-n-Heptyloxyphenyl)phenyl)-6-ethylphthalonitrile.
3-(p-(4'-n-Heptyloxyphenyl)phenyl)-6-n-propylphthalonitrile.
3-(p-(4'-Methyloxyethyloxyphenyl)phenyl)-6-methylphthalonitrile.
3-(p-(4'-Ethyloxyethyloxyethyloxyphenyl)phenyl)-6-methylphthalonitrile.

EXAMPLE 15

Using 1-(p-(4'-n-propylphenyl)phenyl)-4-methyl-1,3-butadiene and fumaronitrile, 3-(p-(4'-n-propylphenyl)phenyl)-6-methylphthalonitrile was obtained by the same method as in Example 1.

Likewise, the following compounds were obtained.
3-(p-(4'-n-Propylphenyl)phenyl)-6-ethylphthalonitrile.
3-(p-(4'-n-Propylphenyl)phenyl)-6-n-propylphthalonitrile.
3-(p-(4'-n-Propylphenyl)phenyl)-6-n-butylphthalonitrile.
3-(p-(4'-n-Propylphenyl)phenyl)-6-n-pentylphthalonitrile.
3-(p-(4'-n-Pentylphenyl)phenyl)-6-methylphthalonitrile.
3-(p-(4'-n-Pentylphenyl)phenyl)-6-ethylphthalonitrile.
3-(p-(4'-n-Pentylphenyl)phenyl)-6-n-propylphthalonitrile.
3-(p-(4'-n-Pentylphenyl)phenyl)-6-n-butylphthalonitrile.
3-(p-(4'-n-Heptylphenyl)phenyl)-6-ethylphthalonitrile.
3-(p-(4'-n-Heptylphenyl)phenyl)-6-ethylphthalonitrile.
3-(p-(4'-n-Heptylphenyl)phenyl)-6-n-propylphthalonitrile.

EXAMPLE 16

Using 1-(4'-n-propyl-1'-bicyclo(2,2,2)octyl)-4-(p-n-butoxyphenyl)-1,3-butadiene and fumaronitrile, 3-(4'-n-propyl-1'-bicyclo(2,2,2)octyl)-6-(p-n-butoxyphenyl)phthalonitrile was obtained by the same method as in Example 1.

Likewise, the following compounds were obtained.
3-(4'-n-Propyl-1'-bicyclo(2,2,2)octyl)-6-(p-methoxyphenyl)phthalonitrile.
3-(4'-n-Propyl-1'-bicyclo(2,2,2)octyl)-6-(p-ethoxyphenyl)phthalonitrile.
3-(4'-n-Propyl-1'-bicyclo(2,2,2)octyl)-6-(p-n-propyloxyphenyl)phthalonitrile.
3-(4'-n-Propyl-1'-bicyclo(2,2,2)octyl)-6-(p-n-pentyloxyphenyl)phthalonitrile.
3-(4'-n-Propyl-1'-bicyclo(2,2,2)octyl)-6-(p-n-hexyloxyphenyl)phthalonitrile.
3-(4'-n-Propyl-1'-bicyclo(2,2,2)octyl-6-(p-n-heptyloxyphenyl)phthalonitrile.
3-(4'-n-Butyl-1'-bicyclo(2,2,2)octyl)-6-(p-methoxyphenyl)phthalonitrile.
3-(4'-n-Butyl-1'-bicyclo(2,2,2)octyl)-6-(p-ethoxyphenyl)phthalonitrile.
3-(4'-n-Butyl-1'-bicyclo(2,2,2)octyl)-6-(p-n-propyloxyphenyl)phthalonitrile.
3-(4'-n-Butyl-1'-bicyclo(2,2,2)octyl)-6-(p-n-butoxyphenyl)phthalonitrile.
3-(4'-n-Butyl-1'-bicyclo(2,2,2)octyl)-6-(p-n-pentyloxyphenyl)phthalonitrile.
3-(4'-n-Butyl-1'-bicyclo(2,2,2)octyl)-6-(p-n-hexyloxyphenyl)phthalonitrile.
3-(4'-n-Butyl-1'-bicyclo(2,2,2)octyl)-6-(p-n-heptyloxyphenyl)phthalonitrile.
3-(4'-n-Pentyl-1'-bicyclo(2,2,2)octyl)-6-(p-methoxyphenyl)phthalonitrile.
3-(4'-n-Pentyl-1'-bicyclo(2,2,2)octyl)-6-(p-ethoxyphenyl)phthalonitrile.
3-(4'-n-Pentyl-1'-bicyclo(2,2,2)octyl)-6-(p-n-propyloxyphenyl)phthalonitrile.
3-(4'-n-Pentyl-1'-bicyclo(2,2,2)octyl)-6-(p-n-butoxyphenyl)phthalonitrile.
3-(4'-n-Pentyl-1'-bicyclo(2,2,2)octyl)-6-(p-n-pentyloxyphenyl)phthalonitrile.
3-(4'-n-Pentyl-1'-bicyclo(2,2,2)octyl)-6-(p-n-hexyloxyphenyl)phthalonitrile.
3-(4'-n-Pentyl-1'-bicyclo(2,2,2)octyl)-6-(p-n-Heptyloxyphenyl)phthalonitrile.
3-(4'-n-Hexyl-1'-bicyclo(2,2,2)octyl)-6-(p-methoxyphenyl)phthalonitrile.
3-(4'-n-Hexyl-1'-bicyclo(2,2,2)octyl)-6-(p-ethoxyphenyl)phthalonitrile.
3-(4'-n-Hexyl-1'-bicyclo(2,2,2)octyl)-6-(p-n-propyloxyphenyl)phthalonitrile.
3-(4'-n-Hexyl-1'-bicyclo(2,2,2)octyl)-6-(p-n-butoxyphenyl)phthalonitrile.
3-(4'-n-Hexyl-1'-bicyclo(2,2,2)octyl)-6-(p-n-pentyloxyphenyl)phthalonitrile.
3-(4'-n-Hexyl-1'-bicyclo(2,2,2)octyl)-6-(p-n-hexyloxyphenyl)phthalonitrile.
3-(4'-n-Hexyl-1'-bicyclo(2,2,2)octyl)-6-(p-n-heptyloxyphenyl)phthalonitrile.
3-(4'-n-Heptyl-1'-bicyclo(2,2,2)octyl)-6-(p-methoxyphenyl)phthalonitrile.
3-(4'-n-Heptyl-1'-bicyclo(2,2,2)octyl)-6-(p-ethoxyphenyl)phthalonitrile.
3-(4'-n-Heptyl-1'-bicyclo(2,2,2)octyl)-6-(p-n-propyloxyphenyl)phthalonitrile.
3-(4'-n-Heptyl-1'-bicyclo(2,2,2)octyl)-6-(p-n-butoxyphenyl)phthalonitrile.
3-(4'-n-Heptyl-1'-bicyclo(2,2,2)octyl)-6-(p-n-pentyloxyphenyl)phthalonitrile.
3-(4'-n-Heptyl-1'-bicyclo(2,2,2)octyl)-6-(p-n-hexyloxyphenyl)phthalonitrile.
3-(4'-n-Heptyl-1'-bicyclo(2,2,2)octyl)-6-(p-n-heptyloxyphenyl)phthalonitrile.

EXAMPLE 17

Using 1-(4'-n-Propyl-1'-bicyclo(2,2,2)octyl)-4-n-pentyl-1,3-butadiene and fumaronitrile, 3-(4'-n-propyl-1'-bicyclo(2,2,2)octyl)-6-n-pentylphthalonitrile was obtained by the same method as in Example 1.

Likewise, the following compounds were obtained.

3-(4'-n-Propyl-1'-bicyclo(2,2,2)octyl)-6-ethylphthalonitrile.
3-(4'-n-Propyl-1'-bicyclo(2,2,2)octyl)-6-n-propylphthalonitrile.
3-(4'-n-Propyl-1'-bicyclo(2,2,2)octyl)-6-n-butylphthalonitrile.
3-(4'-n-Propyl-1'-bicyclo(2,2,2)octyl)-6-n-hexylphthalonitrile.
3-(4'-n-Propyl-1'-bicyclo(2,2,2)octyl)-6-n-heptylphthalonitrile.
3-(4'-n-Butyl-1'-bicyclo(2,2,2)octyl)-6-ethylphthalonitrile.
3-(4'-n-Butyl-1'-bicyclo(2,2,2)octyl)-6-n-propylphthalonitrile.
3-(4'-n-Butyl-1'-bicyclo(2,2,2)octyl)-6-n-butylphthalonitrile.
3-(4'-n-Butyl-1'-bicyclo(2,2,2)octyl)-6-n-pentylphthalonitrile.
3-(4'-n-Butyl-1'-bicyclo(2,2,2)octyl)-6-n-hexylphthalonitrile.
3-(4'-n-Pentyl-1'-bicyclo(2,2,2)octyl)-6-methylphthalonitrile.
3-(4'-n-Pentyl-1'-bicyclo(2,2,2)octyl)-6-n-propylphthalonitrile.
3-(4'-n-pentyl-1'-bicyclo(2,2,2)octyl)-6-n-butylphthalonitrile.
3-(4'-n-Pentyl-1'-bicyclo(2,2,2)octyl)-6-n-pentylphthalonitrile.
3-(4'-n-Hexyl-1'-bicyclo(2,2,2)octyl)-6-ethylphthalonitrile.
3-(4'-n-Hexyl-1'-bicyclo(2,2,2)octyl)-6-n-propylphthalonitrile.
3-(4'-n-Hexyl-1'-bicyclo(2,2,2)octyl)-6-n-butylphthalonitrile.
3-(4'-n-Hexyl-1'-bicyclo(2,2,2)octyl)-6-n-pentylphthalonitrile.
3-(4'-n-Heptyl-1'-bicyclo(2,2,2)octyl)-6-ethylphthalonitrile.
3-(4'-n-Heptyl-1'-bicyclo(2,2,2)octyl)-6-n-propylphthalonitrile.
3-(4'-n-Heptyl-1'-bicyclo(2,2,2)octyl)-6-n-butylphthalonitrile.
3-(4'-n-Heptyl-1'-bicyclo(2,2,2)octyl)-6-n-pentylphthalonitrile.

EXAMPLE 18

Using 1-(p-(4'-n-pentyl-1'-bicyclo(2,2,2)octyl)phenyl)-4-(trans-4'-n-pentylcyclohexyl)-1,3-butadiene and fumaronitrile, 3-(p-(4'-n-pentyl-1'-bicyclo(2,2,2)octyl)phenyl)-6-(trans-4'-n-pentylcyclohexyl)phthalonitrile was obtained by the same method as in Example 1.

Likewise, the following compounds were obtained.
3-(p-(4'-n-Propyl-1'-bicyclo(2,2,2)octyl)phenyl)-6-(trans-4'-n-propylcyclohexyl)phthalonitrile.
3-(p-(4'-n-Propyl-1'-bicyclo(2,2,2)octyl)phenyl)-6-(trans-4''-n-butylcyclohexyl)phthalonitrile.
3-(p-(4'-n-Propyl-1'-bicyclo(2,2,2)octyl)phenyl)-6-(trans-4''-n-pentylcyclohexyl)phthalonitrile.
3-(p-(4'-n-Pentyl-1'-bicyclo(2,2,2)octyl)phenyl)-6-(trans-4''-n-propylcyclohexyl)phthalonitrile.
3-(p-(4'-n-Pentyl-1'-bicyclo(2,2,2)octyl)phenyl)-6-(trans-4''-n-butylcyclohexyl)phthalonitrile.
3-(p-(4'-n-Heptyl-1'-bicyclo(2,2,2)octyl)phenyl)-6-(trans-4''-n-propylcyclohexyl)phthalonitrile.

EXAMPLE 19 (APPLICATION EXAMPLE 1)

A mixture of 20.0 parts of trans-4-n-propylcyclohexanecarboxylic acid-p-n-pentyloxyphenyl ester, 20.0 parts of trans-4-pentylcyclohexanecarboxylic acid p-n-ethoxyphenyl ester, 30.0 parts of trans-4-n-pentylcyclohexanecarboxylic acid p-n-pentyloxyphenyl ester and 30.0 parts of p-methoxybenzoic acid p'-n-pentylphenyl ester had a nematic liquid crystal temperature range of $-6°-65°$ C. and $\Delta\epsilon$ of $-0.9$. A mixture prepared by blending 0.50 g of 3-(p-methoxyphenyl)-6-(p'-n-heptyloxyphenyl)phthalinitrile obtained in Example 2 with 9.0 g of the above described mixture as a base solution crystal had a liquid crystal temperature range of $-5°-66°$ C. and $\Delta\epsilon$ of $-2.0$.

1% by weight of the dye D-16 produced by BDH Co. as a guest was added to the resulted mixture as a host. When a guest-host effect was examined, the threshold voltage was 2.4 V and the saturation voltage was 2.9. In case of measuring those of the base liquid crystal itself, they were 10 V or more, respectively.

EXAMPLE 20 (APPLICATION EXAMPLE 2)

3-(p-n-butoxyphenyl)-6-methylphthalonitrile obtained in Example 4 was used under the same condition as in Example 19 instead of the compound obtained in Example 2. When the guest-host effect was examined, the threshold voltage was 2.3 V and the saturation voltage was 2.7 V.

EXAMPLE 21 (APPLICATION EXAMPLE 3)

3-Cyclohexyl-6-(trans-4'-n-propylcyclohexyl)phthalonitrile obtained in Example 9 was used under the same condition as in Example 19 instead of the compound obtained in Example 2. When the guest-host effect was examined, the threshold voltage was 2.2 V and the saturation voltage was 2.6 V.

REFERENCE EXAMPLE 1

Viscosity of the compounds of the present invention and that of known phthalonitrile compounds were compared. Namely, the viscosity of liquid crystal compositions obtained in Examples 20 and 21 and that of liquid crystal compositions which were obtained by adding compounds shown in the following Table 1 in such an amount that the threshold voltage became the same value, instead of phthalonitrile derivatives of the present invention were measured by the conventional method. The results are shown in Table 1.

TABLE 1

| No. | Phthalonitrile derivative | Threshold voltage | Viscosity (20° C.) |
|---|---|---|---|
| 1 | Compound in Example 20 | 2.3 V | 36 cp |
| 2 | Compound in Example 21 | 2.2 V | 38 cp |
| 3 | (n)H₁₁C₅—⟨H⟩—CO₂—⟨⟩—OC₃H₇(n) with CN, CN substituents | 2.6 V | 42 cp |

TABLE 1-continued

| No. | Phthalonitrile derivative | Threshold voltage | Viscosity (20° C.) |
|---|---|---|---|
| 4 | 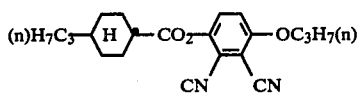 | 2.3 V | 48 cp |

As be obvious from the above results, the compounds of the present invention have a characteristic of greatly improving the drawback of the prior known materials, that is, they have a low viscosity, namely, responce speed can be increased without changing other properties, as compared with the prior known materials.

REFERENCE EXAMPLE 2

Liquid crystal temperature range of compounds of the present invention and that of the known phthalonitrile compound were compared. Namely, liquid crystal compositions were prepared by the same method as in Example 19, except that 0.5 parts of phthalonitrile compounds of the present invention obtained in Examples 4, 6 and 2 and the known compound

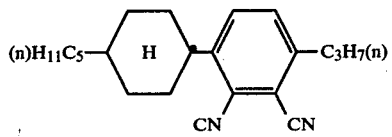

to 9.5 parts of the same base liquid crystal as in Example 19, respectively. The liquid temperature range of them are shown in Table 2.

TABLE 2

| No. | Composition | Liquid crystal temperature range |
|---|---|---|
| 1. | Compound of Example 4 | 0–58° C. |
| | (n)H$_9$C$_4$O—⟨⟩—⟨⟩—CH$_3$ with CN CN | |
| 2. | Compound of Example 6 | −5–65° C. |
| | (n)H$_{11}$C$_5$—⟨⟩—⟨⟩—⟨H⟩—C$_3$H$_7$(n) with CN CN | |
| 3. | Compound of Example 2 | −5–66° C. |
| | H$_3$CO—⟨⟩—⟨⟩—⟨⟩—OC$_7$H$_{15}$(n) with CN CN | |
| 4. | (n)H$_{11}$C$_5$—⟨H⟩—⟨⟩—C$_3$H$_7$(n) with CN CN | 2–48° C. |

As be obvious, a wider liquid crystal temperature range could be obtained by using the compound of the present invention.

In a liquid crystal display device using a liquid crystal composition having a wide liquid crystal temperature range, a temperature range capable of displaying becomes wide. Accordingly, it is obvious that the compounds of the present invention are superior to the above described known compound.

While the invention has been described in detail and with reference to specific embodiments thereof, it will be apparent to one skilled in the art that various changes and modifications can be made therein without departing from the spirit and scope thereof.

What is claimed is:

1. Phthalonitrile derivatives represented by the formula (I):

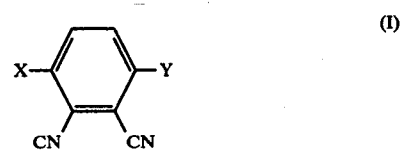

(I)

(wherein X and Y each represents an alkyl group having 1 to 9 carbon atoms, an alkoxy group having 1 to 9 carbon atoms,

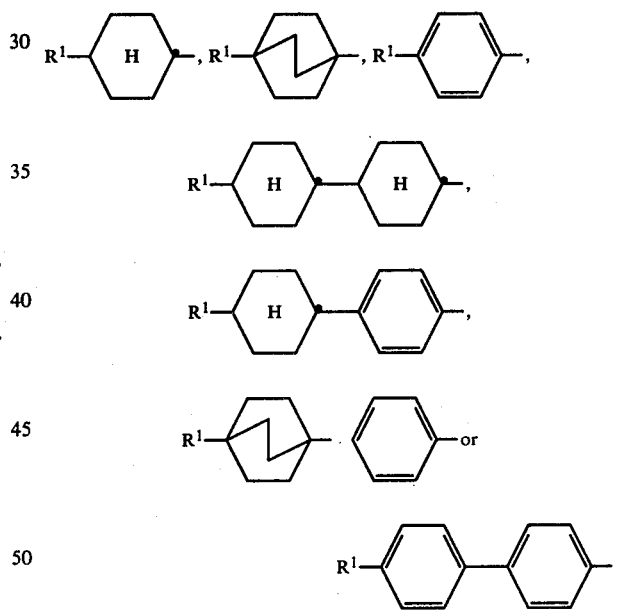

(wherein $R^1$ represents a hydrogen atom, —C$_m$H$_{2m+1}$, —O—(CH$_2$CH$_2$O)$_n$—C$_m$H$_{2m+1}$,

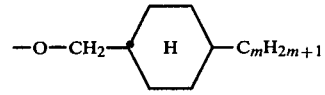

or a halogen atom, wherein m represents an integer of 1 to 9 and n represents 0, 1 or 2), but at least one of X and Y does not represent a methyl group, and Y does not represent an alkyl group having 1 to 9 carbon atoms or an alkoxy group having 1 to 9 carbon atoms in the case that X represents

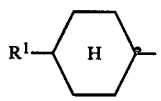

and $R^1$ represents an alkyl group having 1 to 9 carbon atoms).

2. Phthalonitrile derivatives according to claim 1 represented by the formula (II):

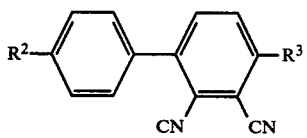

(wherein $R^2$ represents a hydrogen atom, an alkyl group having 1 to 9 carbon atoms, an alkoxy group having 1 to 9 carbon atoms, a halogen atom,

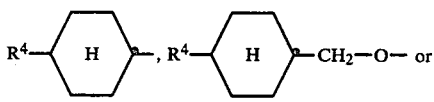

and $R^3$ represents an alkyl group having 1 to 9 carbon atoms or

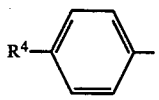

(wherein $R^4$ represents a hydrogen atom, an alkyl group having 1 to 9 carbon atoms or an alkoxy group having 1 to 9 carbon atoms)).

3. Phthalonitrile derivatives according to claim 2 represented by the formula (II'):

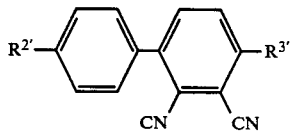

(wherein $R^{2'}$ represents an alkyl group having 1 to 9 carbon atoms or an alkoxy group having 1 to 9 carbon atoms, and $R^{3'}$ represents an alkyl group having 1 to 9 carbon atoms or

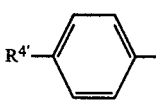

(wherein $R^{4'}$ represents an alkyl group having 1 to 9 carbon atoms or an alkoxy group having 1 to 9 carbon atoms)).

4. Phthalonitrile derivatives according to claim 1 represented by the formula (III):

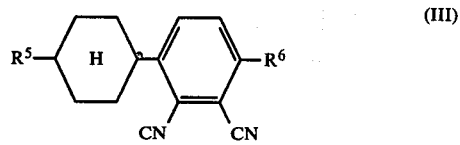

(wherein $R^5$ represents a hydrogen atom, an alkyl group having 1 to 9 carbon atoms, an alkoxy group having 1 to 9 carbon atoms or

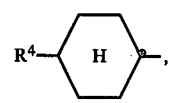

and $R^6$ represents an alkyl group having 1 to 9 carbon atoms, an alkoxy group having 1 to 9 carbon atoms,

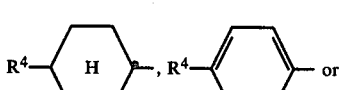

or

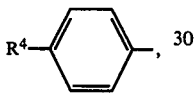

(wherein $R^4$ represents a halogen atom, a hydrogen atom, an alkyl group having 1 to 9 carbon atoms or an alkoxy group having 1 to 9 carbon atoms), but $R^6$ does not represent an alkyl group having 1 to 9 carbon atoms or an alkoxy group having 1 to 9 carbon atoms in case that $R^5$ represents an alkyl group having 1 to 9 carbon atoms).

5. Phthalonitrile derivatives according to claim 4 represented by the formula (III'):

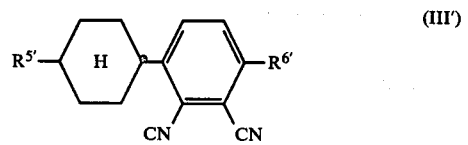

(wherein $R^{5'}$ represents a hydrogen atom, an alkyl group having 1 to 9 carbon atoms or an alkoxy group having 1 to 9 carbon atoms, and $R^{6'}$ represents

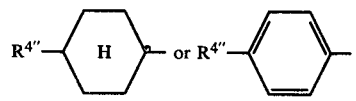

(wherein $R^{4''}$ represents a halogen atom, an alkyl group having 1 to 9 carbon atoms or an alkoxy group having 1 to 9 carbon atoms)).

6. Phthalonitrile derivatives according to claim 1 represented by the formula (IV):

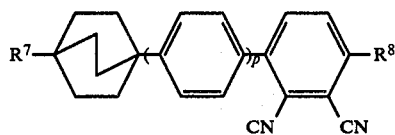 (IV)

(wherein $R^7$ represents an alkyl group having 1 to 9 carbon atoms, $R^8$ represents an alkyl group having 1 to 9 carbon atoms, an alkoxy group having 1 to 9 carbon atoms,

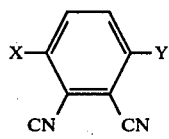

(wherein $R^4$ represents a hydrogen atom, an alkyl group having 1 to 9 carbon atoms or an alkoxy group having 1 to 9 carbon atoms), and p represents 0 or 1).

7. A liquid crystal composition comprising at least two components, at least one of which is a phthalonitrile derivative represented by the Formula (I):

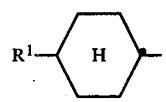 (I)

(wherein X and Y each represents an alkyl group having 1 to 9 carbon atoms, an alkoxy group having 1 to 9 carbon atoms

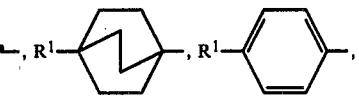

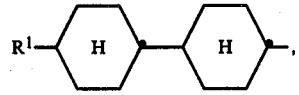

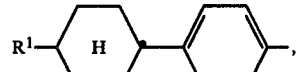

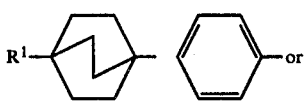

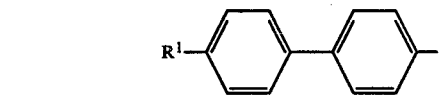

(wherein $R^1$ represents a hydrogen atom, $-C_mH_{2m+1}$, $-O-(CH_2CH_2O)_n-C_mH_{2m+1}$,

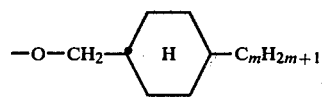

or a halogen atom, wherein m represents an integer of 1 to 9 and n represents 0, 1 or 2), but at least one of X and Y does not represent a methyl group, and Y does not represent an alkyl group having 1 to 9 carbon atoms or an alkoxy group having 1 to 9 carbon atoms in the case that X represents

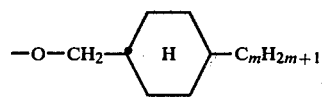

and $R^1$ represents an alkyl group having 1 to 9 carbon atoms).

* * * * *